(12) United States Patent
Huang

(10) Patent No.: US 10,578,456 B2
(45) Date of Patent: Mar. 3, 2020

(54) SAFETY ENHANCED COMPUTER ASSISTED DRIVING METHOD AND APPARATUS

(71) Applicant: Intel Corporation, Santa Clara, CA (US)

(72) Inventor: Jinshi Huang, Fremont, CA (US)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 15/938,492

(22) Filed: Mar. 28, 2018

(65) Prior Publication Data

US 2019/0049267 A1    Feb. 14, 2019

(51) Int. Cl.

| | |
|---|---|
| *G01C 21/36* | (2006.01) |
| *B60W 40/09* | (2012.01) |
| *A61B 5/18* | (2006.01) |
| *G06N 3/02* | (2006.01) |
| *G06N 20/00* | (2019.01) |
| *B60W 40/08* | (2012.01) |
| *A61B 5/16* | (2006.01) |

(52) U.S. Cl.
CPC ............ *G01C 21/3697* (2013.01); *A61B 5/18* (2013.01); *B60W 40/09* (2013.01); *G06N 3/02* (2013.01); *G06N 20/00* (2019.01); *A61B 5/165* (2013.01); *B60W 2040/0827* (2013.01)

(58) Field of Classification Search
CPC ............ G01C 21/3697; G01C 21/3415; A61B 5/165; A61B 5/09; A61B 5/18; A61B 5/02055; A61B 5/7267; G06F 15/18; G06N 3/02; G06N 20/00; B60W 2040/0827; B60W 50/14; B60W 40/09; B60W 2540/18; B60W 2520/10; B60W 2510/0638; B60W 2510/0604

USPC ..................................... 340/573.1, 575, 576
See application file for complete search history.

(56) References Cited

U.S. PATENT DOCUMENTS

| | | |
|---|---|---|
| 5,797,134 A | 8/1998 | McMillan et al. |
| 7,937,278 B1 | 5/2011 | Cripe et al. |
| 8,630,768 B2 | 1/2014 | McClellan et al. |
| 8,849,501 B2 | 9/2014 | Cook et al. |

(Continued)

OTHER PUBLICATIONS

International Search Report and Written Opinion dated Jun. 4, 2019 for International Patent Application No. PCT/US2019/018793; 10 pages.

*Primary Examiner* — Brian Wilson
(74) *Attorney, Agent, or Firm* — Schwabe, Williamson & Wyatt, P.C.

(57) ABSTRACT

Methods and apparatuses for safety enhanced computer-assisted driving. In embodiments, an apparatus for computer-assisted driving may include a neural network to determine a classification for behavior of a driver of a vehicle having the apparatus, based at least in part on data about the vehicle collected in real time, and a current level of stress or drowsiness of the driver determined in real time; and a safety action engine coupled to the neural network to determine a safety related action, based at least in part on the determined driver behavior classification and data related to current traffic or road condition of a route the vehicles is currently traveling on. The safety related action may be performed by an infotainment system or a navigation system of the vehicle to assist the driver in driving the vehicle in a safer manner.

20 Claims, 12 Drawing Sheets

(56) References Cited

U.S. PATENT DOCUMENTS

| | | | |
|---|---|---|---|
| 8,854,199 B2 | 10/2014 | Cook et al. | |
| 9,134,731 B2 | 9/2015 | Healey et al. | |
| 2015/0254955 A1* | 9/2015 | Fields | G08B 21/02 |
| | | | 705/4 |
| 2015/0258995 A1 | 9/2015 | Essers et al. | |
| 2015/0272473 A1 | 10/2015 | Zafiroglu et al. | |
| 2015/0302718 A1 | 10/2015 | Konigsberg | |
| 2016/0093210 A1* | 3/2016 | Bonhomme | G08G 1/0967 |
| | | | 340/905 |
| 2016/0283963 A1 | 9/2016 | Zafiroglu et al. | |
| 2017/0032673 A1* | 2/2017 | Scofield | G08G 1/0112 |
| 2017/0337438 A1* | 11/2017 | el Kaliouby, Jr. | A61B 5/0077 |
| 2018/0174457 A1* | 6/2018 | Taylor | B60W 40/09 |

* cited by examiner

| Population Percentages | 5% | 20% | 50% | | 20% | 5% |
|---|---|---|---|---|---|---|
| Safety Level | Dangerous | Unsafe | Target Zone | | Unsafe | Dangerous |
| Characteristics | Too Slow, Unconfident, Disturbs Traffic Flow, Unpredictable | Always Obeys Speed Limits Regardless of Traffic Flow, Not Instinctive Over Scan | Follow Traffic Flow, Predictable, Confident, Proper Scanning Technique | | Routinely Speed, Tailgate, Under Scan | Too Fast, Over Confident Disturbs Traffic Flow, Unpredictable |
| Behavior Classification | Timid ~1002 | Cautious ~1004 | Conservative ~1006 | Neutral ~1008 | Assertive ~1010 | Aggressive ~1012 |
| Drivers | 2nd Std Dev | 1st Std Dev | Mean | | 1st Std Dev | 2nd Std Dev |

Figure 10

SAFETY ENHANCED COMPUTER ASSISTED DRIVING METHOD AND APPARATUS

TECHNICAL FIELD

The present disclosure relates to the field of computer-assisted driving, in particular, to computer assistance for enhancing driving safety.

BACKGROUND

The background description provided herein is for the purpose of generally presenting the context of the disclosure. Unless otherwise indicated herein, the materials described in this section are not prior art to the claims in this application and are not admitted to be prior art by inclusion in this section.

According to the reports by the US National Highway Traffic Safety Administration (NHTSA), 35,092 people died and 2.44 million people were injured in crashes on U.S. roadways. Among the reasons for critical pre-crash event attributed to drivers are the recognition error, decision error, and performance error. A large portion of these errors are related to driving behaviors of the drivers. It is believed the relationship between driver behaviors and driver errors are generally applicable also to driving outside the U.S.

In the past four decades, significant progresses have been made in the safety design of the vehicles, e.g., seat belts, air bags, collapsible steering columns, and so forth have been introduced. In recent years, these progresses further included computer-assisted driving, such as anti-lock brakes, anti-skid and so forth. Among these progresses are the introductions of the On-Board Diagnostic (OBD) port and the subsequent On-Board Diagnostic II (OBD-II) port, which has been used extensively in collecting data for vehicle diagnostics and computer-assisted driving. These design improvements, together with other measures, have contributed to the steady decline of the traffic fatality rate from 5.30 to 1.12 per 100 million Vehicle Miles Traveled (VMT). But more can be done to enhance driving safety.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

FIG. 10 illustrates an example driver behavior classification, in accordance with various embodiments.

DETAILED DESCRIPTION

Figure 1:
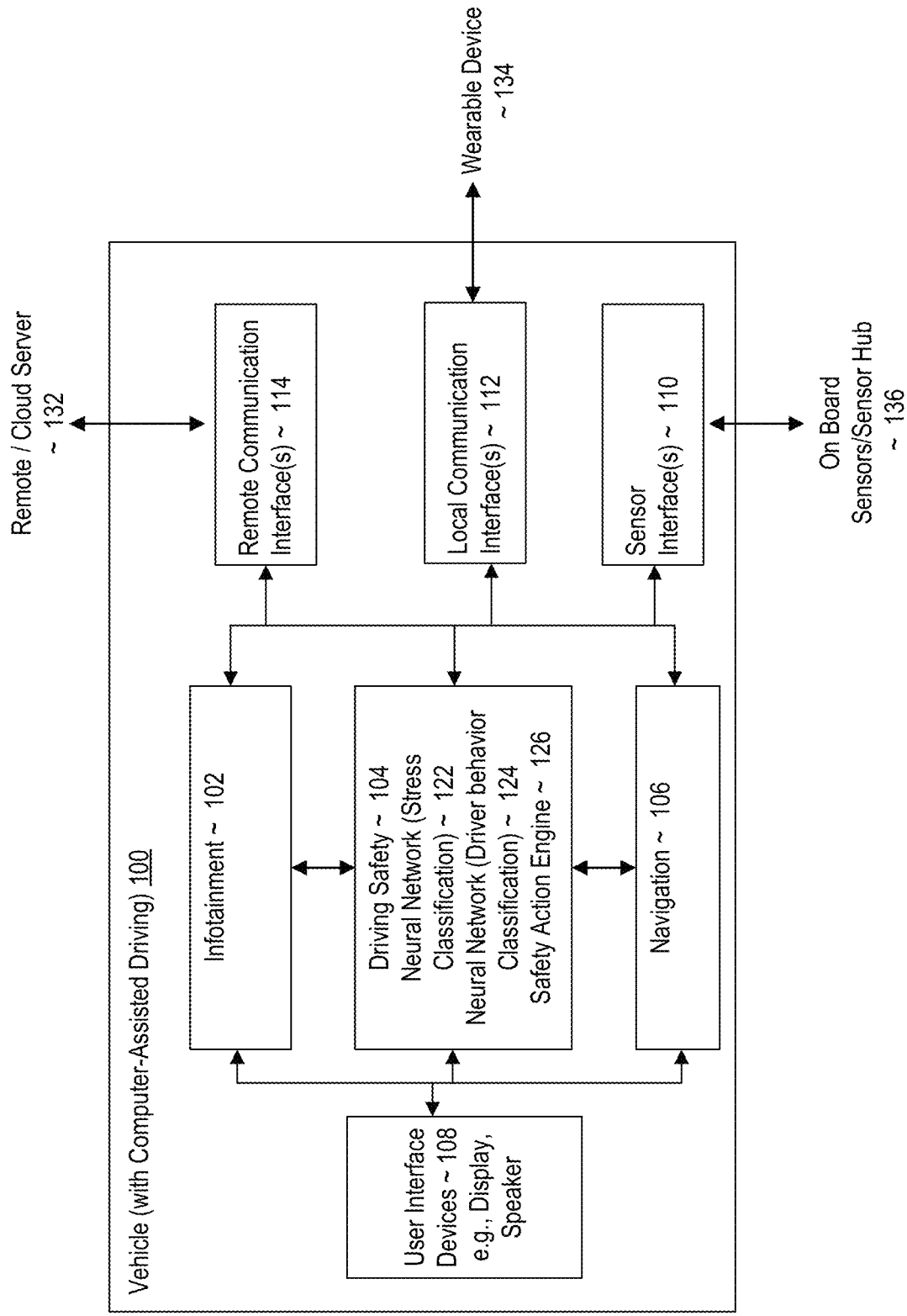
FIG. 1 illustrates an overview of an example arrangement of in-vehicle systems having a driving safety system of the present disclosure, in accordance with various embodiments.

The present disclosure presents methods and apparatuses for safety enhanced computer-assisted driving. In embodiments, an apparatus for computer-assisted driving may include a neural network to determine a classification for behavior of a driver of a vehicle having the apparatus, based at least in part on data about the vehicle collected in real time, and a current level of stress or drowsiness of the driver determined in real time; and a safety action engine coupled to the neural network to determine a safety related action, based at least in part on the determined driver behavior classification and data related to current traffic or road condition of a route the vehicles is currently traveling on. The safety related action may be performed by an infotainment system or a navigation system of the vehicle to assist the driver in driving the vehicle in a safer manner.

In the description to follow, reference is made to the accompanying drawings, which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Operations of various methods may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiments. Various additional operations may be performed and/or described operations may be omitted, split or combined in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

As used hereinafter, including the claims, the terms "interface" and "engine" may refer to, be part of, or include an Application Specific Integrated Circuit (ASIC), an electronic circuit, a programmable combinational logic circuit (e.g., field programmable gate arrays (FPGA)), a processor (shared or dedicate) and/or memory (shared or dedicated) that execute a plurality of programming instructions of one or more software or firmware programs to provide the described functionality.

Referring now to FIG. 1, wherein an overview of an example arrangement of in-vehicle systems having a driving safety system of the present disclosure, in accordance with various embodiments, is illustrated. As shown, in embodiments, vehicle 100 equipped with computer-assisted driving technology may include a number of on-board systems, components and interfaces 102-114. In particular, vehicle 100 may include infotainment system 102, navigation system 106, and driving safety system 104 incorporated with teachings of the present disclosure to provide enhanced driving safety. Except for the cooperation with driving safety system 104 described below, infotainment system 102 and navigation system 106 may be any one of these systems known in the art. In embodiments, driving safety system 104 may include neural network 124 configured to classify behaviors of a driver of vehicle 100 in real time, and safety action engine 126 to generate safety action, based at least in part on the driver behavior classifications, to enhance driving safety of vehicle 100 in real time. In embodiments, safety action engine 126 further generate safety action, based on traffic and environment conditions of a route vehicle 100 is traveling.

In embodiments, neural network 124 may be initially trained by a machine learning system with a simulation driving environment. Further, neural network 124 may be configured to adapt via self-learning, during field usage, enabling a more personalized and optimized solution to individual drivers. In embodiments, driver behavior classifications may include a timid class of drivers, a cautious class of drivers, a conservative class of drivers, a neutral class of drivers, an assertive class of drivers and an aggressive class of drivers. In embodiments, safety actions may include causing: playing stress-relieving music, alerting for caution, suggesting rest, or suggesting alternative route.

For the illustrated embodiments, driving safety system 104 may further include neural network 122 to classify and output, in real time, stress or drowsiness levels of the driver of vehicle 100, based at least in part on physiological data of the driver, collected in real time. In embodiments, neural network 122 may respectively classify each of stress and drowsiness of the driver of the vehicle into one of 10 levels. In alternate embodiments, neural network 122 may be disposed on wearable device 134 worn by a driver of vehicle 100. Similar to neural network 124, in embodiments, neural network 122 may be initially trained by a machine learning system with a simulation driving environment. Likewise, neural network 122 may be configured to adapt via self-learning, during field usage, enabling a more personalized and optimized solution to individual drivers.

These and other aspects of driving safety system 104 and wearable device 134 will be described in further detail below with references to the remaining figures, after other components of vehicle 100, such as user interface device 108 and sensor/communication interfaces 110-114 had been described. But before describing user interface device 108 and sensor/communication interfaces 110-114, it should be noted that vehicle 100 is described as having infotainment system 102, navigation system 106, and driving safety system 104, merely for ease of understanding. In embodiments, infotainment system 102, navigation system 106, and driving safety system 104 may be considered as one single combined in-vehicle system, while in other embodiments, one or more of infotainment system 102, navigation system 106, and driving safety system 104 may be considered as a combination of one or more other systems/subsystems. In other words, the demarcations between infotainment system 102, navigation system 106, and driving safety system 104 are arbitrary, and as mentioned before, merely for ease of understanding.

As described earlier, in addition to infotainment system 102, navigation system 106, and driving safety system 104, vehicle 100 may further include one or more user interface devices 108, and one or more sensor/communication interfaces 110-112. Except for its cooperation with infotainment system 102, navigation system 106, and/or driving safety system 104, user interface devices 108 may be any one of a number of such devices known in the art. Examples of such user interface devices 108 may include but are not limited to a display (which may be touch sensitive), speakers, microphone, cursor control device, and so forth.

An example of sensor/communication interfaces 110-114 may include one or more sensor interfaces 110 to interface with one or more sensors or sensor hubs (also referred to as telematics devices) of vehicle 100 to receive, in real time, data associated with vehicle 100 sensed by the various sensors disposed on vehicle 100. Another example of sensor/communication interfaces 110-114 may include one or more local communication interfaces 112 to interface with a wearable device worn by a driver of vehicle 100 to receive, in real time, physiological data associated with the driver of vehicle 100 sensed by the various sensors of the wearable device, or stress/drowsiness level classifications determined based on the physiological data of the driver collected by the various sensors of the wearable device. The former is suitable for embodiments where neural network 122 to determine stress/drowsiness level classification for the driver is disposed with driving safety system 104, while the latter is suitable for embodiments where neural network 122 is disposed with wearable device 134 worn by the driver of vehicle 100. Still another example of sensor/communication interfaces 110-114 may include one or more communication interfaces 114 to receive, in real time, from one or more remote/cloud servers 132, traffic and other environment data associated with a route vehicle 100 is traveling on. In embodiments, one or more communication interfaces 114 may also be used to receive social networking and/or entertainment content.

Examples of data associated with vehicle 100 sensed by the various sensors disposed on vehicle 100 may include, but are not limited to, miles driven, time of day, vehicle speed, engine speed (RPM), throttle position, acceleration, engine load, brake pressure, sharp turns, and steering wheel angle, and so forth. Examples of physiological data associated with the driver of vehicle 100 sensed by the various sensors of the wearable device may include but are not limited to: galvanic skin response (GSR) data, or data indicative of the drowsiness of the driver.

In embodiments, sensor interface(s) 110 may be one or more OBD-II compatible interfaces. In other embodiments, sensor interface(s) 110 may be one or more $I^2C$, Industry Standard Architecture (ISA), or Universal Serial Bus (USB) interfaces. In embodiments, local communication interface(s) 110 may be one or more Bluetooth®, Near Field Communication (NFC) or USB interfaces. In embodiments, remote communication interface(s) 114 may be one or more Cellular or WiFi interfaces.

During operation, driving safety system 104 may receive, in real time, vehicle data (via sensor interface(s) 110), physiological data or stress/drowsiness level classification of the driver of vehicle 100 (via local communication interface(s) 112), and traffic and/or environment data of the route vehicle 100 is traveling on (via remote communication interface(s) 114). For embodiments where driving safety system 104 receives, in real time, physiological data of the driver of vehicle 100, neural network 122 may process the physiological data to generate, in real time, the stress/drowsiness level classification of the driver of vehicle 100. On availability of the stress/drowsiness level classification of the driver of vehicle 100, neural network 124 may be employed to generate, in real time, the behavior classification of the driver of vehicle 100, based at least in part on the received vehicle data, and the determined stress/drowsiness level classification of the driver of vehicle 100. On determination of the behavior classification of the driver of vehicle 100, safety action engine 126 may generate, in real time, safety actions for infotainment system 102 and/or navigation system 106, to implement/perform to enhance the safety of driving of vehicle 100.

In embodiments, driving safety system 104 may further include a self-learning module (not shown) to adapt neural network 122 and/or 124 via self-learning, using datasets collected during field use. Initial training and subsequent adaptation via self-learning will be further described later.

Figure 2:
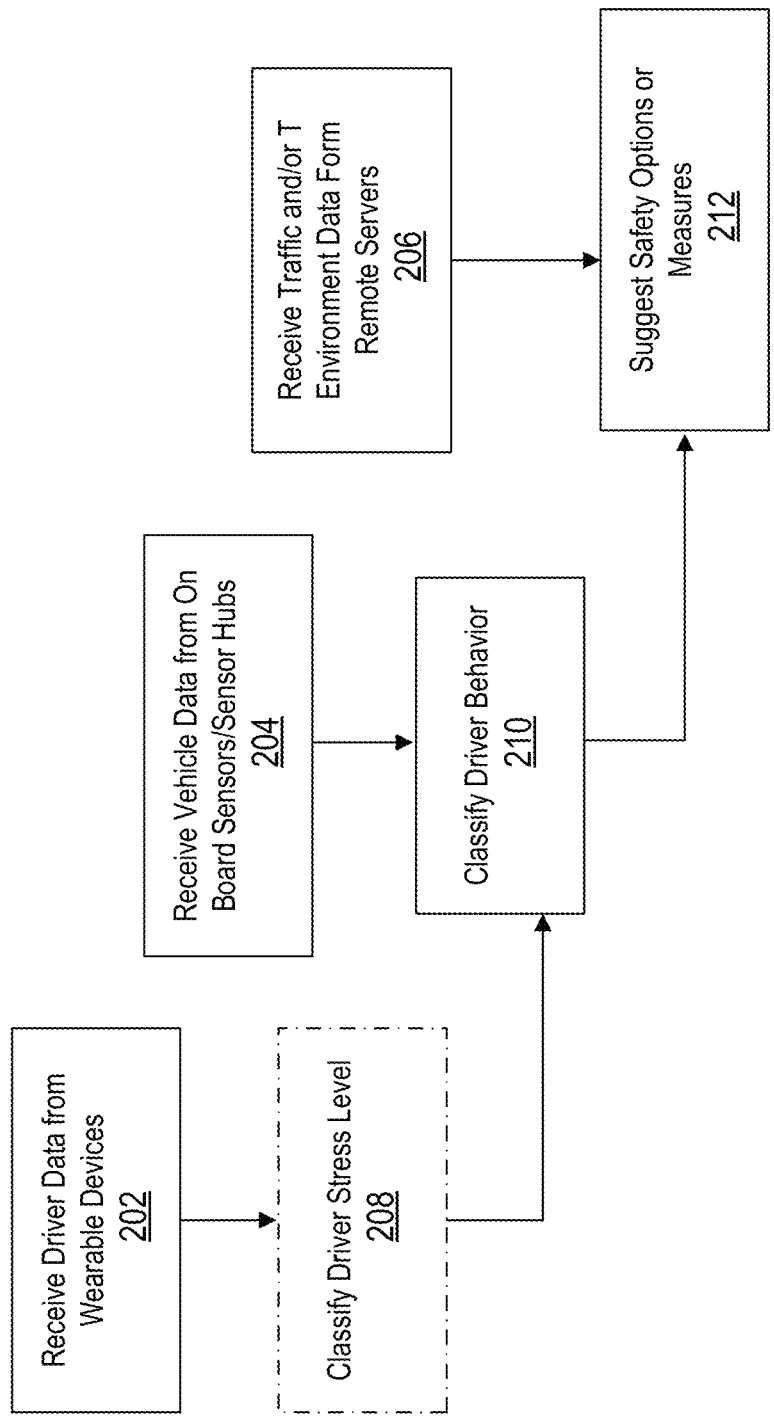
FIG. 2 illustrates an overview of an example process of enhancing driving safety, in accordance with various embodiments.

Referring now to FIG. 2, wherein an overview of an example process of enhancing driving safety of a vehicle, in accordance with various embodiments, is illustrated. As shown, process 200 for enhancing driving safety of a vehicle may include operations performed at blocks 202-212. The operations may be performed by e.g., driving safety system 104 of FIG. 1. In alternate embodiments, process 200 may include more or less operations, or with some of the operations combined or sub-divided.

Process 200 may start at block 202, 204 and/or 206. At block 202, driver data may be received from a wearable device worn by the driver of vehicle 100. The wearable device having at least sensors to collect, in real time, physiological data of the driver. In some embodiments, the received driver data may be the real time collected physiological data. In other embodiments, the wearable device may include a neural network configured to process the physiological data to generate, in real time, a stress/drowsiness level classification of the driver. For these embodiments, the received driver data may be the stress/drowsiness level classification of the driver determined in real time. For the embodiments where physiological data are received, from block 202, process 200 may proceed to block 208. At block 208, the physiological data may be processed to generate, in real time, a stress/drowsiness level classification of the driver. For the embodiments where a stress and/or a drowsiness level classification of the driver is received, from block 202, process 200 may proceed to block 210, skipping block 208.

At block 204, vehicle data may be received from on board sensors or sensor hubs. From blocks 202/208 and block 204, process 200 may proceed to block 210. At block 210, the behavior of the driver of vehicle 100 may be classified based at least in part on the stress/drowsiness level classification of the driver and the vehicle data of the vehicle.

From blocks 210 and 206, process 200 may proceed to block 212. At block 212, safety options or measures may be generated, in real time, based at least in part of the behavior of the driver, determined in real time, and the traffic/environment data of the route received.

Figure 3:
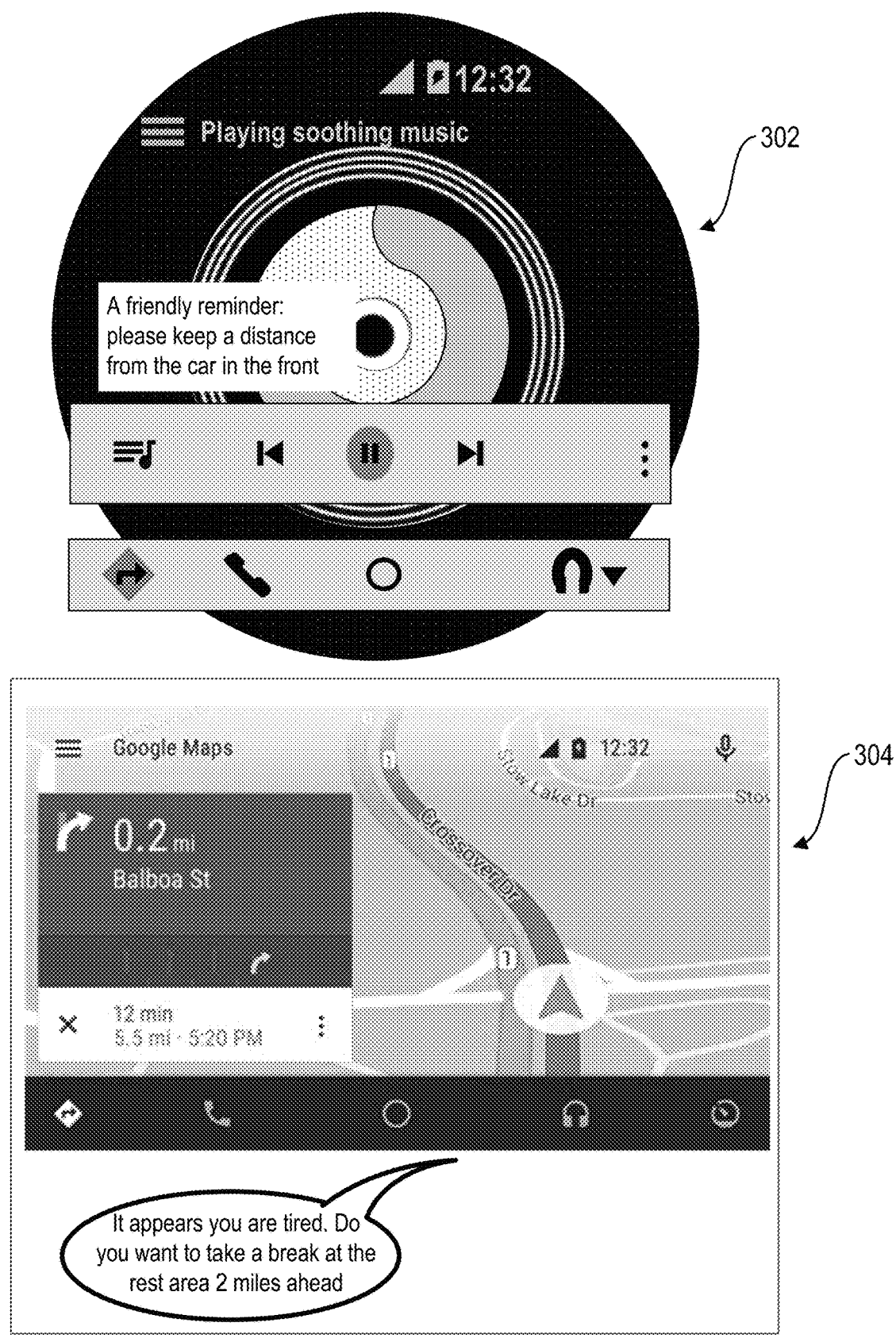
FIG. 3 illustrates a number of example safety related actions, in accordance with various embodiments.

Referring now to FIG. 3, wherein a number of example safety related actions, in accordance with various embodiments, are illustrated. These are illustrative non-limiting examples. The top portion of FIG. 3, illustrates a first example safety action 302, where the driving safety engine determined to request the infotainment system to play soothing music, in view of the real time determined driver behavior and real time received traffic/environment condition of the route the vehicle is on. First example safety action 302, as shown, may also include a safety reminder for the driver, e.g., a reminder to keep a distance from the car in front.

The lower portion of FIG. 3, illustrates another example safety action 304, where the driving safety engine determined to request the navigation system to suggest to the driver to take a break, in view of the driver being determined to be tired, and the traffic/environment data received. In other words, the stress/drowsiness level of a driver to trigger a safety action may vary depending on the traffic/road condition, e.g., a relatively lower stress/drowsiness level of a driver may trigger a safety action in a heavy traffic, raining and/or winding road condition, whereas a relatively higher stress/drowsiness level of a driver may need to be detected before triggering a safety action in a light traffic, sunny and/or interstate highway condition.

Figure 4:
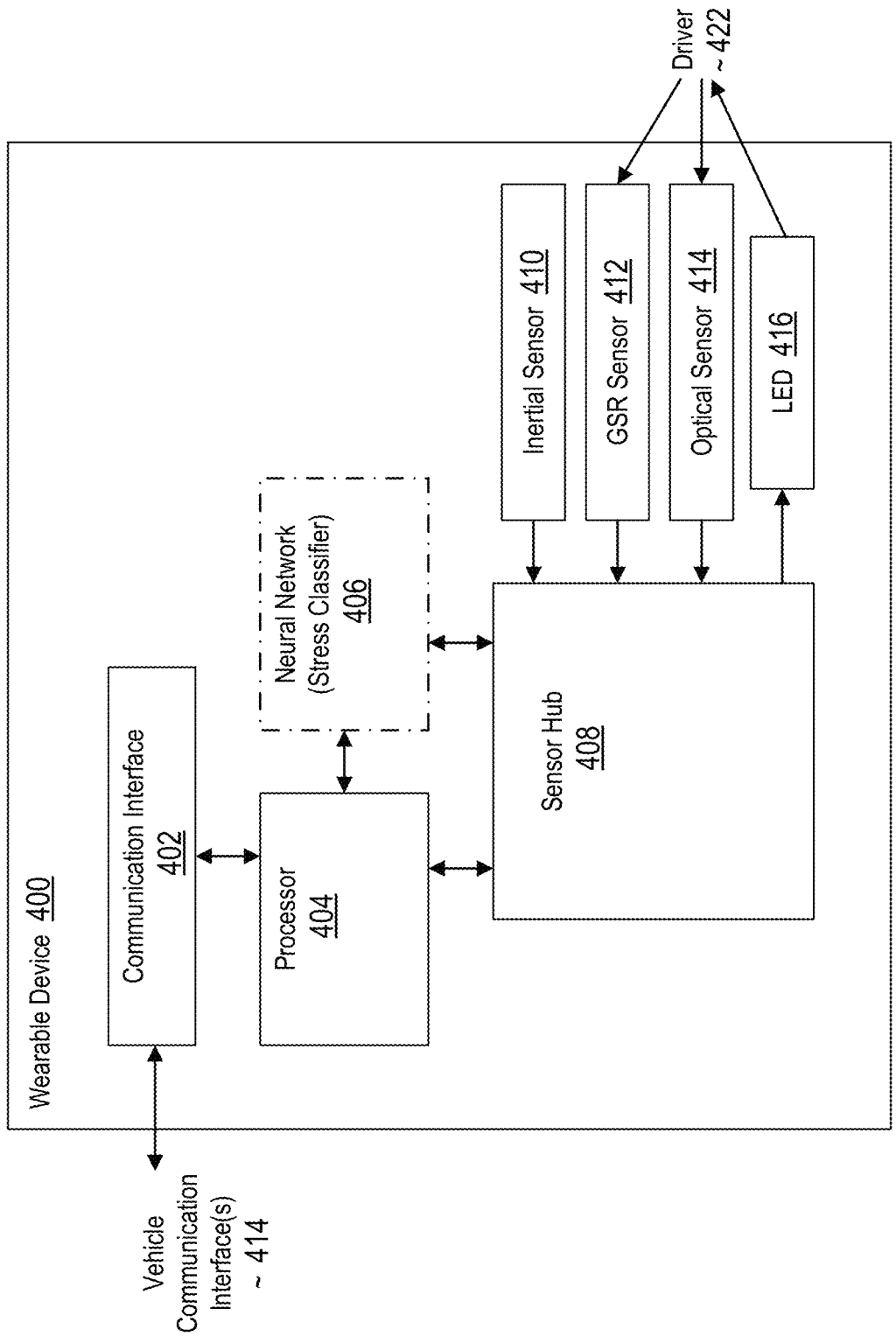
FIG. 4 illustrates an example implementation of a wearable device, in accordance with various embodiments.

Referring now to FIG. 4, wherein an example implementation of a wearable device, in accordance with various embodiments, is illustrated. As shown, for the illustrated embodiments, wearable device 400, which may be wearable device 134, may include communication interface 402, processor 404, optional neural network 406, sensor hub 408, inertial sensor 410, Galvanic skin response (GSR) sensor 412, optical sensor 414 and light emitting diodes (LED) 416.

Inertial sensor 410, GSR sensor 412, optical sensor 414 and/or LED 416 may be configured to collect, in real time, physiological data of driver 422 of the vehicle. In particular, GSR sensor 412 may be configured to collect GSR data for stress level determination, and optical sensor 414 in conjunction with LED 416 may be configured to collect heart rate data of the driver based on electrocardiogram (ECG) data of the driver. Sensor hub 408 may be configured to control operation of inertial sensor 410, GSR sensor 412 and/or optical sensor 414, including e.g., pre-processing, normalizing, and/or aggregating the raw sensor data collected by inertial sensor 410, GSR sensor 412 and/or optical sensor 414. In particular, sensor hub 408 may be configured to split GSR signal into the skin conductance level (SCL) component, and the skin conductance response (SCR) component. In embodiments, sensor hub 408 may configured to sample the GSR signal at 15-20 Hz, with the cut-off frequency of a low pass filter (LPF) set at 5 Hz to filter out noise.

Neural network 406, if provided, as described earlier, may be configured to process the physiological data of driver 422 of the vehicle (such as heart rate and GSR signals), and generate, in real time, a stress/drowsiness level classification of the driver 422 of the vehicle. As described earlier for neural network 122, neural network 406 may respectively classify each of stress and drowsiness of the driver of the vehicle into one of 10 levels. Similarly, neural network 406 may be initially trained via machine learning in a simulated driving environment. Further neural network 406 may be configured to be self-adapted via self-learning, enabling more personalized and optimized service to a wearer of wearable device 400. Communication interface 402 may be configured to communicate with the outside world, e.g., in the provision of either physiological data or derived stress level classification of driver 422 of the vehicle to vehicle communication interface 424 of the vehicle. Vehicle communication interface 424 may be local communication interface 112 of FIG. 1.

Processor 404 may be configured to control the overall operation of wearable device 400, including the operation of neural network 406, sensor hub 408, and/or communication interface 402. In embodiments, processor 404 may be any processor known in the art, including but not limited to the various microprocessors and/or microcontrollers available from Intel Corporation, Santa Clara, Calif.

In embodiments, wearable device 400 may be a head mounted device, such as a helmet, or a pair of eyeglasses. In other embodiments, wearable device 400 may be a wrist worn device, such as a smartwatch. In still other embodiments, wearable device 400 may be a body worn device, such as smart clothing.

Figure 5:
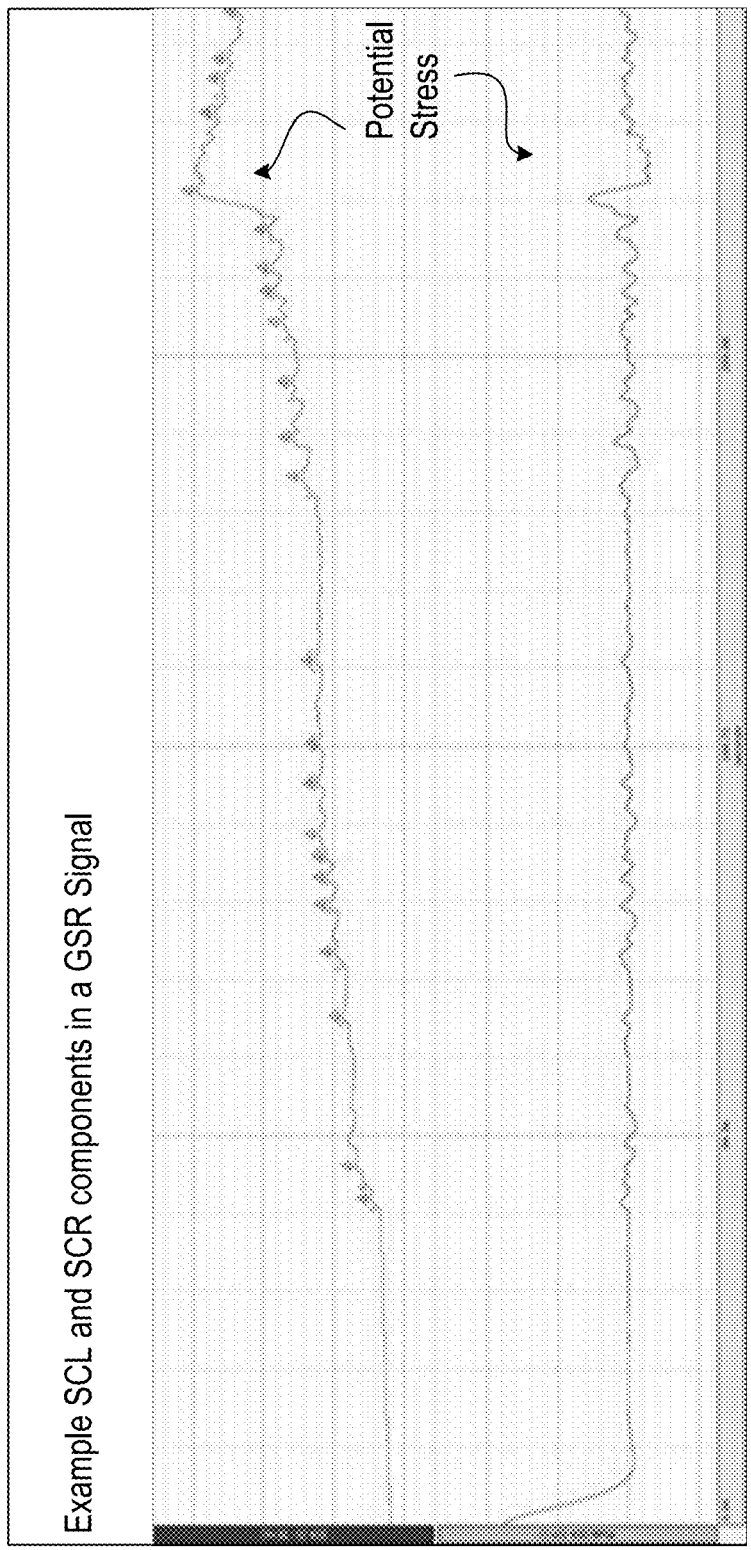
FIG. 5 illustrates example driver related data provided by the wearable device, in accordance with various embodiments.

Referring now to FIG. 5, wherein example driver related data provided by the wearable device, in accordance with various embodiments, are shown. Shown are an example skin conductance level (SCL) component, and an example skin conductance response (SCR) component of the GSR signal. As illustrated, stress level of the driver may be inferred by the abnormal spikes in the SCL and SCR signal components of the GSR signal.

Figure 6:
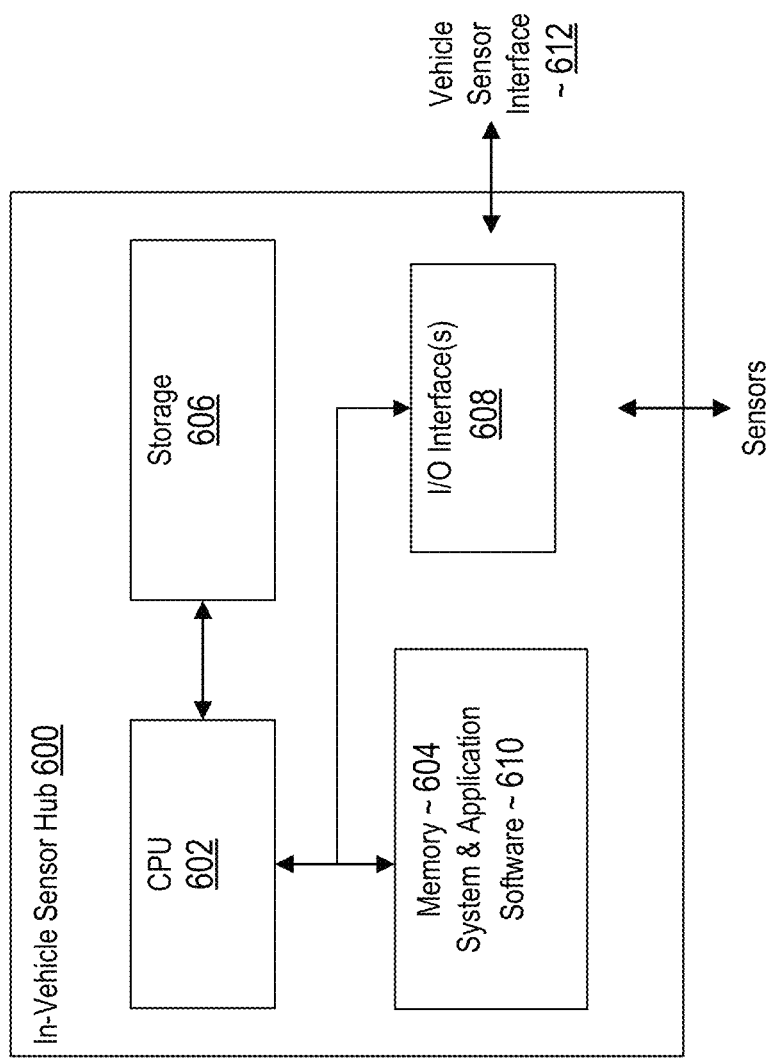
FIG. 6 illustrates an example implementation of an in-vehicle sensor hub, in accordance with various embodiments.

Referring now to FIG. 6, wherein an example implementation of an in-vehicle sensor hub, in accordance with various embodiments, is illustrated. As shown, in-vehicle sensor hub (also referred to as a telematics device) 600 may include CPU 602, memory 604 having system and application software 610, storage 606, and one or more input/output (I/O) interface 608. I/O interface(s) 608, as described earlier, may be configured to interface with the on-board sensors of the vehicle at one end, and to vehicle sensor interface 612 (which may be vehicle sensor interface 110 of FIG. 1). Except for their use to provide vehicle related data to driving safety system 104, CPU 602, memory 604, software 610, storage 606, and I/O interface(s) 608, may be any one of these elements known in the art.

Figure 7:
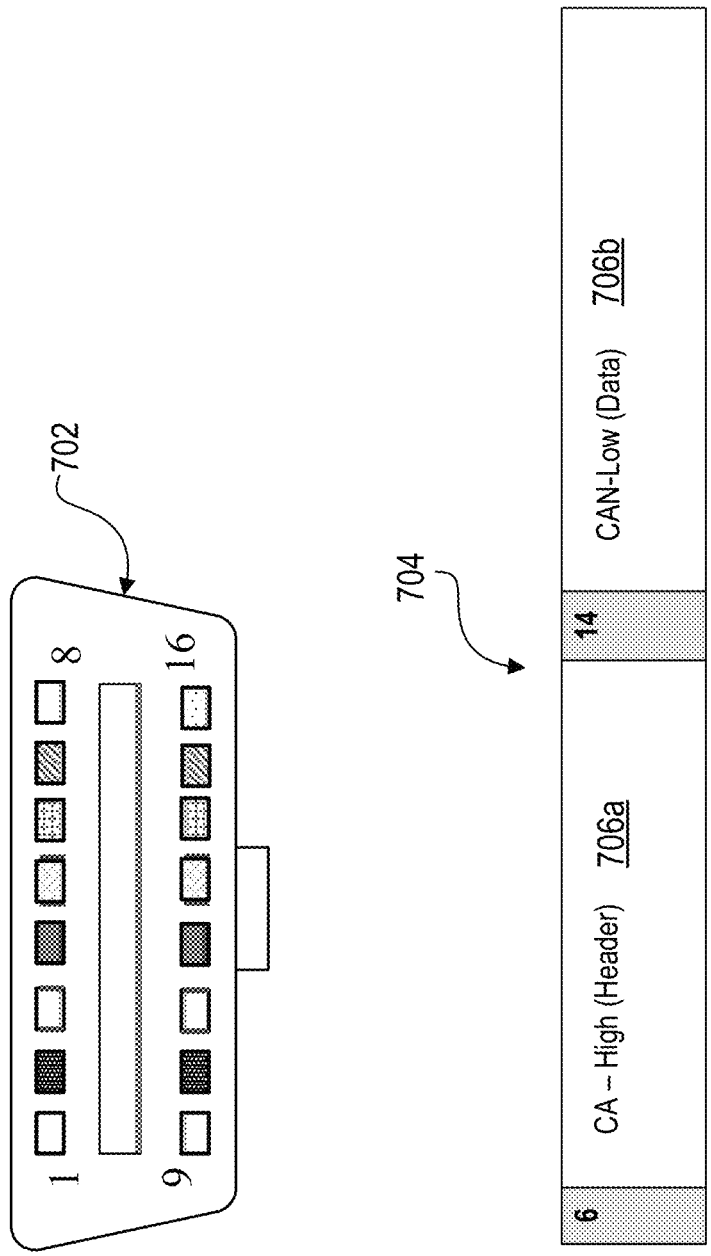
FIG. 7 illustrates an example OBD-II port, and an example data packet, in accordance with various embodiments.

Referring now to FIG. 7, wherein an example OBD-II port and an example data packet, in accordance with various embodiments, are illustrated. As shown, example OBD-II port 702 may include 16 pins for transmitting data packets 706 of the sensed vehicle data in accordance with the automobile controller area network (CAN) protocol. Each data packet 706 may include a first header portion 706a, referred to as the CAN-High portion, and a second data portion 706b, referred to as the CAN-Low portion. The portions are specified in Society of Automotive Engineering (SAE) J2284/3_201611 High-Speed CAN (HSC) dated 2016 Nov. 29, and International Organization for Standardization (ISO) 15765 Road vehicles—Diagnostic communication over Controller Area Network (DoCAN) dated 2016. The OBD-II data can be decoded via OBD-II Mode01 operation with appropriate Parameter IDs (PIDs).

Table I below shows a number of example PIDs and their data:

| PID | Data | Description | Unit | Formula# |
|---|---|---|---|---|
| 0D | 1 | Vehicle speed | km/ | A |
| 0C | 2 | Engine speed | rpm | ((A*256) + B) |
| 11 | 1 | Throttle | % | A*100/255 |
| 04 | 1 | Engine load | % | A*100/255 |

Figure 8:
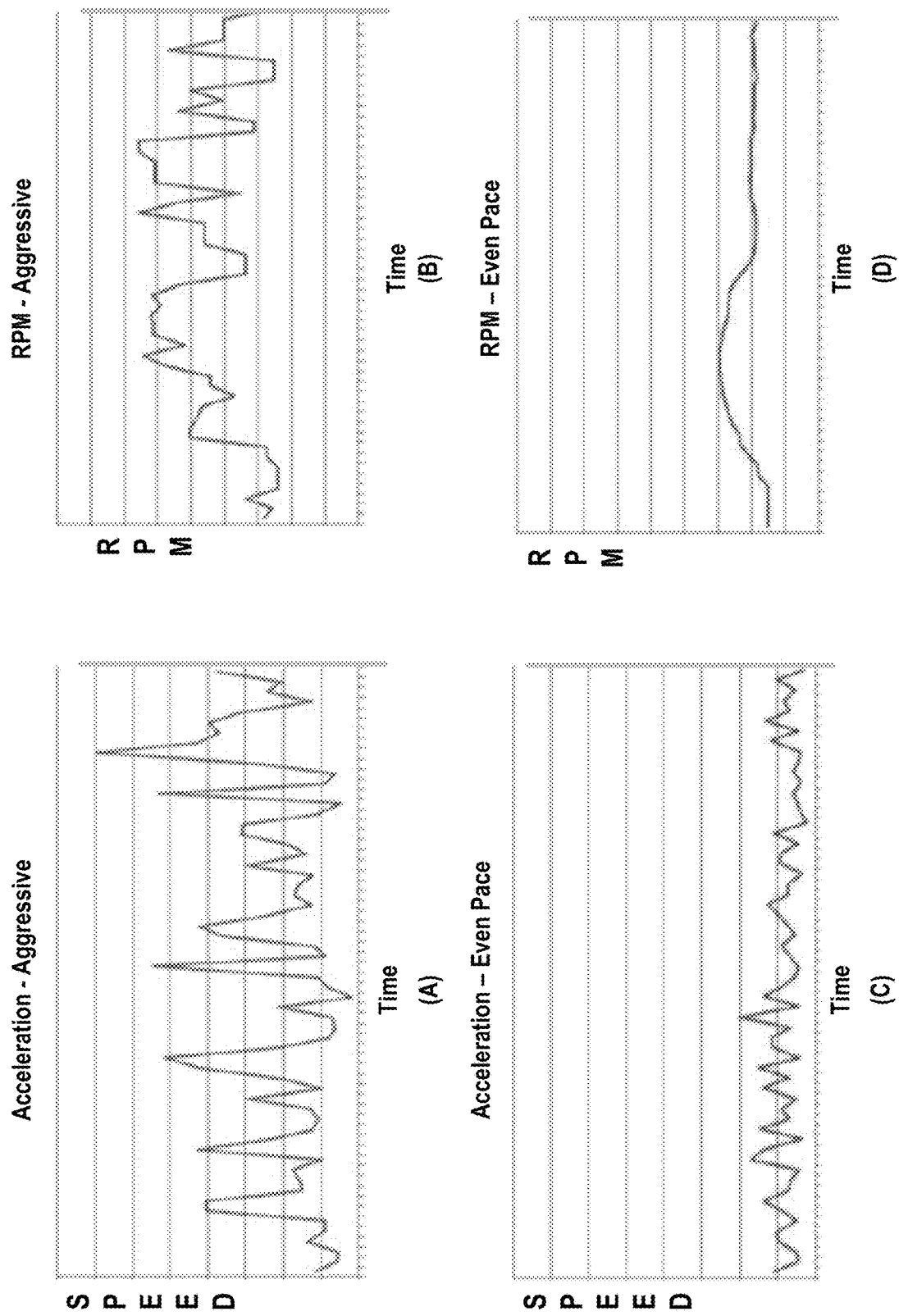
FIG. 8 illustrates example driving characteristics of different classes of drivers, in accordance with various embodiments.

Referring now to FIG. 8, wherein example driving characteristics of different classes of drivers, in accordance with various embodiments, are illustrated. Example graph 802a illustrates an acceleration speed vs time plot for an aggressive driver, whereas example graph 802c illustrates an acceleration speed vs time plot for an even pace driver. Example graph 802b illustrates an engine revolution per minute (RPM) vs time plot for an aggressive driver, whereas example graph 802d illustrates an engine RPM vs time plot for an even pace driver. These different profiles enable neural network 124 to determine the behavior classification of a driver of vehicle 100.

Figure 9:
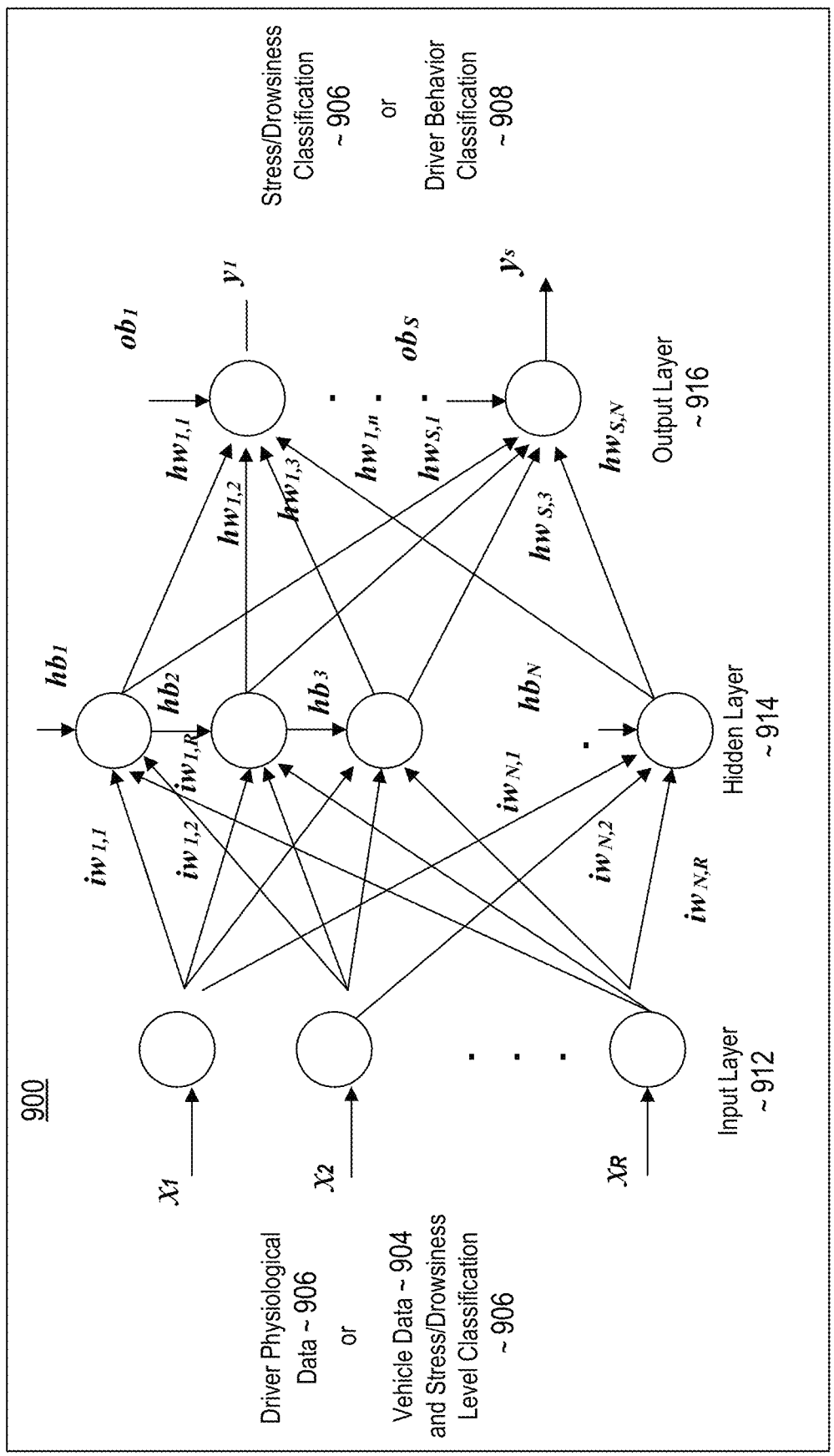
FIG. 9 illustrates an example neural network, in accordance with various embodiments.

Referring now to FIG. 9, wherein an example neural network, in accordance with various embodiments, is illustrated. As shown, neural network, which may be neural network 122 or 124 of FIG. 1 may be a multilayer feedforward neural network comprising an input layer 912, one or more hidden layers 914 and an output layer 916. As a stress/drowsiness level classification neural network, input layer 912 receives driver physiological data ($x_i$) as inputs. Hidden layer(s) 914 processes the inputs, and eventually, output layer 916 outputs the stress/drowsiness level classification 906 ($y_i$) of the driver. As a driver behavior classification neural network, input layer 912 receives vehicle data 904 ($x_i$) and stress/drowsiness level classification data 906 ($x_i$) as inputs. Hidden layer(s) 914 processes the inputs, and eventually, output layer 916 outputs the driver behavior classification 908 ($y_i$) of the driver.

Multilayer feedforward neural network (FNN) may be expressed through the following equations:

$$ho_i = f(\Sigma_{j=1}^{R}(iw_{i,j} x_j) + hb_i), \text{ for } i=1, \ldots, N$$

$$y_i = f(\Sigma_{k=1}^{N}(hw_{i,k} ho_k) + ob_i), \text{ for } i=1, \ldots, S$$

Where $ho_i$ and $y_i$ are the hidden layer variables and the final outputs, respectively. f( ) is typically a non-linear function, such as the sigmoid function or rectified linear (ReLu) function that mimics the neurons of the human brain. R is the number of inputs. N is the size of the hidden layer, or the number of neurons. S is the number of the outputs. In this example, for simplicity of illustration, there is only one hidden layer in the neural network. In some other embodiments, there can be many layers of hidden layers. Furthermore, the neural network can be in some other types of topology, such as Convolution Neural Network (CNN) or Recurrent Neural Network (RNN). One example of implementation is to set the input of the neural network as a vector combining the stress/drowsiness level and the vehicle data, while the output of the neural network as the vector consisting of the driver's behavior classifications:

$$x = \begin{bmatrix} \text{stress level} \\ \text{drowsiness level} \\ \text{miles driven} \\ \text{time of the day} \\ \text{vehicle speed} \\ \text{enginee speed } (RMP) \\ \text{throttle position} \\ \text{acceleration} \\ \text{engine load} \\ \text{brake pressure} \\ \text{steering wheel angle} \end{bmatrix}, y = \begin{bmatrix} \text{timid} \\ \text{cautious} \\ \text{conservative} \\ \text{neutral} \\ \text{assertive} \\ \text{aggressive} \end{bmatrix}$$

The goal of FNN is to minimize an error function E between the network outputs and the desired targets, by adapting the network variables iw, hw, hb, and ob, as follows:

$$E = \Sigma_{k=1}^{m}(E_k), \text{ where } E_k = \Sigma_{p=1}^{S}(t_{kp}-y_{kp})^2$$

Where $y_{kp}$ and $t_{kp}$ are the predicted and the target values of pth output unit for sample k, respectively, and m is the number of samples collected during this period of time.

Referring now to FIG. 10, wherein an example driver behavior classification, in accordance with various embodiments, is illustrated. As shown, drivers within the first standard deviation from the mean (either direction) typically exhibit characteristics of following traffic flow, drive in a predictable and confident manner, and follow proper scanning technique may be classified as a conservative class 1006 of drivers and a neutral class 1008 of drivers. Drivers between the first standard deviation and the second standard deviation (below the mean) typically exhibit characteristics of always obey speed limits regardless of traffic flow, not instinctive, and over scan may be classified as a cautious class 1004 of drivers, whereas drivers between the first standard deviation and the second standard deviation (above the mean) typically exhibit characteristics of routinely speed, often tailgate, and under scan may be classified as an assertive class 1010 of drivers. Both the cautious class 1004 of drivers and the assertive class 1010 of drivers may be considered as unsafe drivers.

Drivers beyond the second standard deviation (below the mean) typically exhibit characteristics of driving too slow, unconfident, disturb traffic flow and unpredictable, may be classified as a timid class 1002 of drivers, whereas drivers beyond the second standard deviation (above the mean) typically exhibit characteristics of driving too fast, over confident, disturbs traffic flow and unpredictable, may be classified as an aggressive class 1012 of drivers. Both the timid class 1002 of drivers and the aggressive class 1012 of drivers may be considered dangerous drivers.

Neural network 124 (and similarly for neural network 122) may be trained in accordance to the following process: (1) collecting training datasets, (2) selecting the neural network structure, (3) selecting transfer functions, (4) selecting a training algorithm, and (5) evaluating the model performance.

In embodiments, the training phase may employ the back-propagation (BP) algorithm. Further, the Cuckoo Search (CS) heuristic algorithm may be employed to alleviate the potential local minima problems of BP-based algorithms. At the end of the training process, the "knowledge package", which includes the flows and software for the processor and the neural network (or the bit stream to program a hardware accelerator (programmable circuit)), may be generated. The knowledge package may then be installed on the driver safety system 104 (or the wearable device 134), which will then be ready for normal use.

Figure 11:
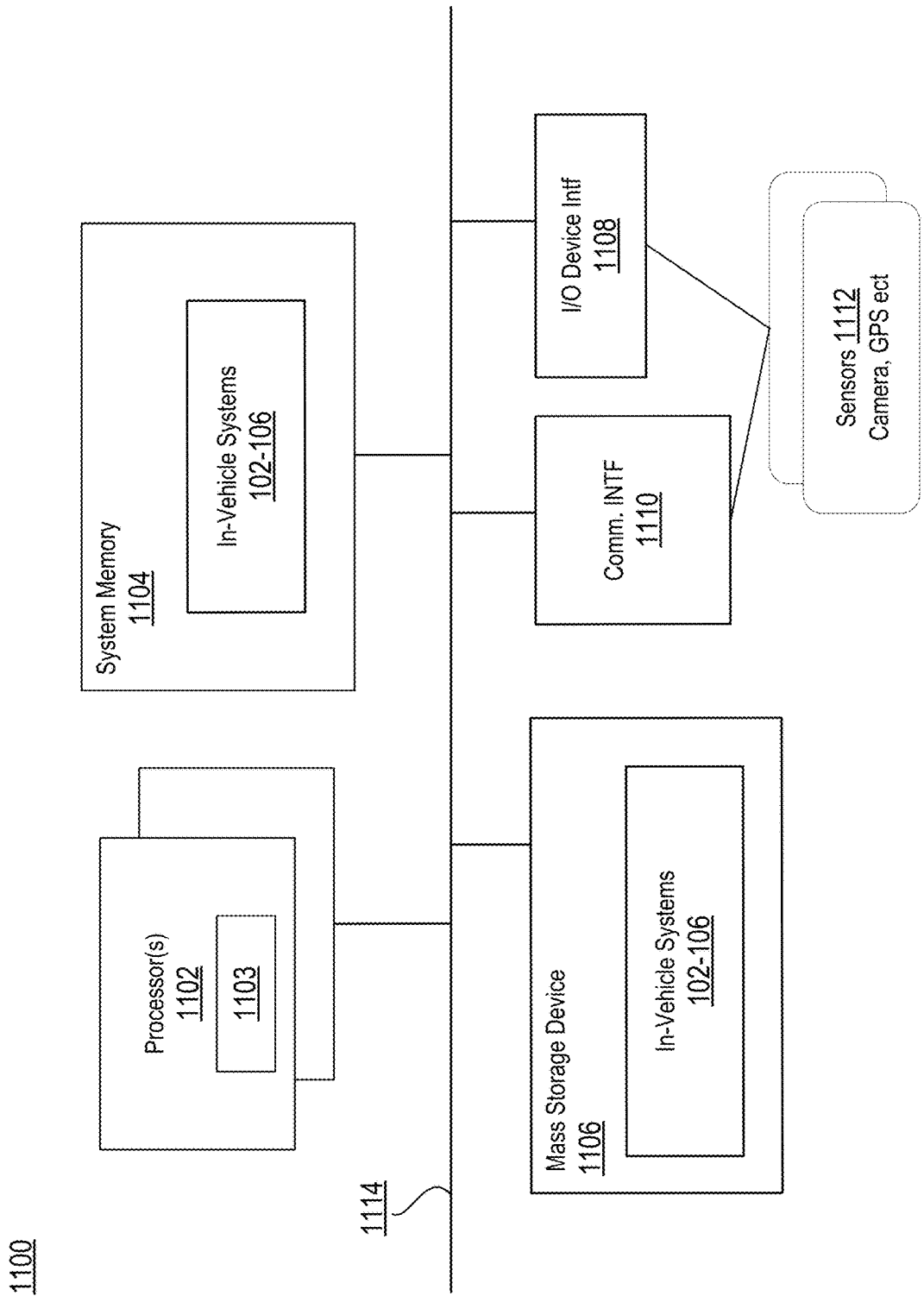
FIG. 11 illustrates an example computer system, suitable for use to practice the present disclosure (or aspects thereof), in accordance with various embodiments.

As described earlier, in embodiments, neural network 122 or 124 may be further configured to be self-learning. During the driving in the field, new datasets may be collected and fed to the self-learning module of the driving safety system 104. The adaptation may be implemented as a semi-supervised learning neural network. Aided by the heuristic rules and the user inputs, the neural network 122/124 will be able to improve its precision (quantified as sensitivity and specificity) gradually. These will enable a more personalized and optimized solution for a driver Referring now to FIG. 11, wherein a block diagram of a computer device suitable for use to practice aspects of the present disclosure, in accordance with various embodiments, is illustrated. As shown, in embodiments, computer device 1100 may include one or more processors 1102 and system memory 1104. Each processor 1102 may include one or more processor cores. In embodiments, one or more processors 1102 may include one or more hardware accelerators 1103 (such as, FPGA). System memory 1104 may include any known volatile or non-volatile memory. Additionally, computer device 1100 may include mass storage device(s) 1106 (such as solid state drives), input/output device interface 1108 (to interface with e.g., cameras, sensors, GPS 1112) and communication interfaces 1110 (such as serial interface, near field communication, network interface cards, modems and so forth). The elements may be coupled to each other via system bus 1114, which may represent one or more buses. In the case of multiple buses, they may be bridged by one or more bus bridges (not shown).

Each of these elements may perform its conventional functions known in the art. In particular, system memory 1104 and mass storage device(s) 1106 may be employed to store a working copy and a permanent copy of the executable code of the programming instructions implementing the operations described earlier, e.g., but are not limited to, operations associated with any one of the in-vehicle systems 102-106 of FIG. 1, in particular, driving safety system 104. The programming instructions may comprise assembler instructions supported by processor(s) 1102 or high-level languages, such as, for example, C, that can be compiled into such instructions. In embodiments, some of the functions, e.g., neural network 122 or 124 may be realized with hardware accelerator 1103 instead.

The permanent copy of the executable code of the programming instructions and/or the bit streams to configure hardware accelerator 1103 may be placed into permanent mass storage device(s) 1106 or hardware accelerator 1103 in the factory, or in the field, through, for example, a distribution medium (not shown), such as a compact disc (CD), or through communication interface 1110 (from a distribution server (not shown)).

Except for the use of computer device 1100 to host in-vehicle systems 102-106, the constitutions of the elements 1110-1114 are otherwise known, and accordingly will not be further described.

Figure 12:
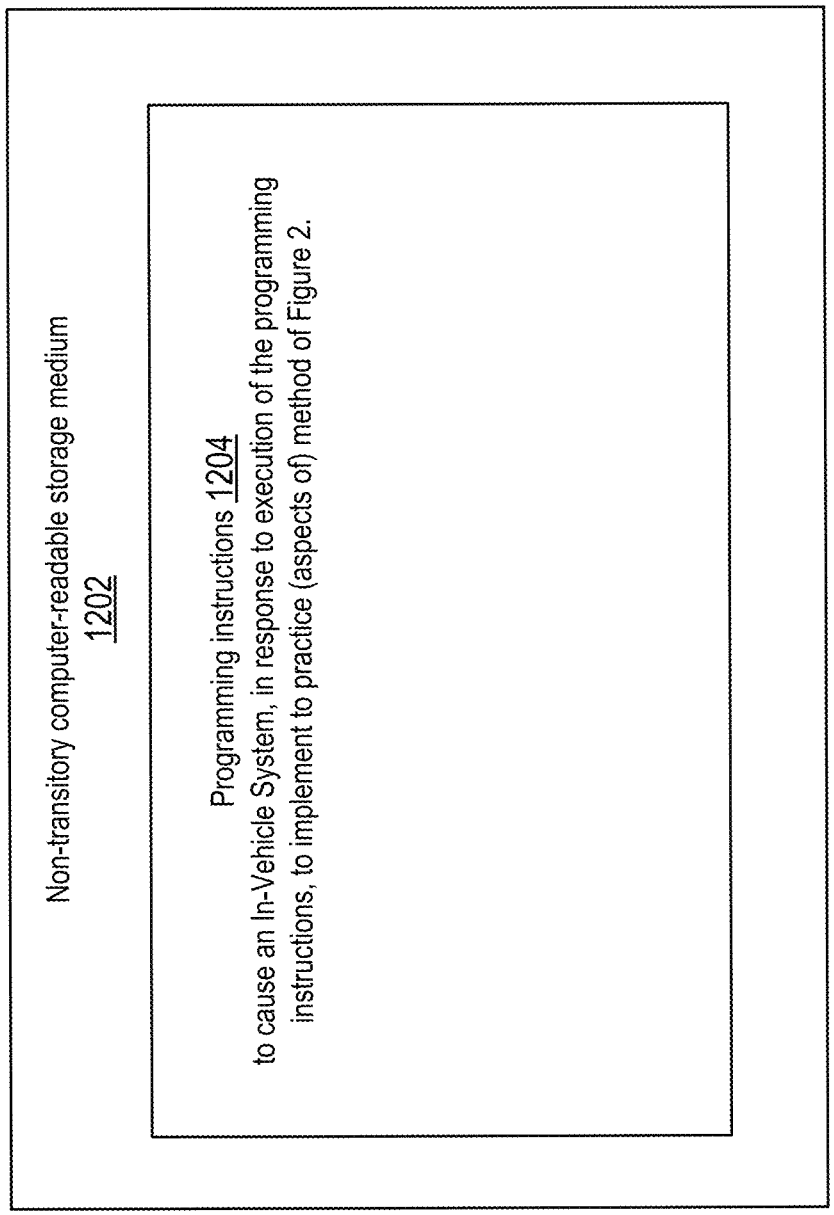
FIG. 12 illustrates an example storage medium with instructions configured to enable a computer system to practice the present disclosure, in accordance with various embodiments.

Referring now to FIG. 12, wherein an example non-transitory computer-readable storage medium having instructions configured to practice all or selected ones of the operations associated with in-vehicle system 102-106 earlier described, in accordance with various embodiments, is shown. As illustrated, non-transitory computer-readable storage medium 1202 may include the executable code of a number of programming instructions 1204. Executable code of programming instructions 1204 may be configured to enable a system, e.g., computer device 1100, in response to execution of the executable code/programming instructions, to perform, e.g., various operations associated with in-vehicle system 102-106, in particular, various operations associated with driving safety system 104. In alternate embodiments, executable code/programming instructions 1204 may be disposed on multiple non-transitory computer-readable storage medium 1202 instead. In still other embodiments, executable code/programming instructions 1204 may be encoded in transitory computer readable medium, such as signals.

In embodiments, a processor may be packaged together with a computer-readable storage medium having some or all of executable code of programming instructions 1204 configured to practice all or selected ones of the operations earlier described. For one embodiment, a processor may be packaged together with such executable code 1204 to form a System in Package (SiP). For one embodiment, a processor may be integrated on the same die with a computer-readable storage medium having such executable code 1204. For one embodiment, a processor may be packaged together with a computer-readable storage medium having such executable code 1204 to form a System on Chip (SoC).

Thus, methods and apparatuses for computer-assisted enhanced driving safety have been described. Example embodiments described include, but are not limited to, the examples to follow.

Example 1 may be an apparatus for computer-assisted driving, comprising: a neural network to determine a classification for behavior of a driver of a vehicle having the apparatus, based at least in part on data about the vehicle collected in real time, and a current level of stress or drowsiness of the driver determined in real time; and a safety action engine coupled to the neural network to determine a safety related action, based at least in part on the determined driver behavior classification and data related to current traffic or road condition of a route the vehicles is currently traveling on. Further, the determined safety related action is performed by an infotainment system or a navigation system of the vehicle to assist the driver in driving the vehicle in a safer manner.

Example 2 may be example 1, wherein the safety related action comprises a selected one of the infotainment system playing soothing music, the infotainment system providing a reminder to the driver to maintain a safe distance from another vehicle ahead of the vehicle, the navigation system suggesting to the driver to take a break at an upcoming location, or the navigation system suggesting to the driver to take an alternative route.

Example 3 may be example 1, wherein the neural network is arranged to determine the behavior of the driver to belong to a timid class of behavior, a cautious class of behavior, a conservative class of behavior, a neutral class of behavior, an assertive class of behavior, or an aggressive class of behavior.

Example 4 may be example 3, wherein the timid class of behavior corresponds to behavior of drivers beyond a negative second standard deviation of a driver profile, a cautious class of behavior corresponds to behavior of drivers between a negative first standard deviation and the negative second standard deviation of the driver profile, the conservative class of behavior corresponds to behavior of drivers between an average and the negative first standard deviation of the driver profile, the neutral class of behavior corresponds to behavior of drivers between the mean and a positive first standard deviation of the driver profile, an assertive class of behavior corresponds to behavior of drivers between the positive first standard deviation and a positive second standard deviation of the driver profile, and the aggressive class of behavior corresponds to behavior of drivers beyond the positive second standard deviation of the driver profile.

Example 5 may be example 1, wherein the neural network is a first neural network, and the apparatus further comprises a second neural network to determine the current level of stress or drowsiness based at least in part on physiological data of the driver collected in real time.

Example 6 may be example 5, wherein at least one of the first neural network, the second neural network is a selected one of a multilayer feedforward neural network, a convolution neural network or a recurrent neural network.

Example 7 may be example 5, wherein at least one of the first neural network, the second neural network or the safety action engine is implemented with a programmable circuit.

Example 8 may be example 5, further comprising a local communication interface to receive the physiological data of the driver from a wearable device worn by the driver, a sensor interface to receive the data about the vehicle collected in real time from a plurality of sensors of the vehicle, or a remote communication interface to receive the data related to current traffic or road condition of the route the vehicle is currently traveling on from one or more cloud servers.

Example 9 may be example 8, wherein the physiological data of the driver comprises galvanic skin response data, components of galvanic skin response data, heart rate or electrocardiogram data of the driver.

Example 10 may be example 8, further comprises the plurality of sensors, and wherein the plurality of sensors include at least a first sensor to sense vehicle speed, a second sensor to sense engine speed, a third sensor to sense throttle position, a fourth sensor to sense engine load, a fifth sensor to sense brake pressure, or a fifth sensor to sense steering wheel angle.

Example 11 may be any one of examples 1-10 further comprising the infotainment system or the navigation system.

Example 12 may be a method for computer assisted driving, comprising: determining a classification for behavior of a driver of a vehicle, based at least in part on data about the vehicle collected in real time, and a current level of stress or drowsiness of the driver determined in real time; and determining a safety related action, based at least in part on the determined driver behavior classification and data related to current traffic or road condition of a route the vehicles is currently traveling on; wherein the determined safety related action is performed by an infotainment system or a navigation system of the vehicle to assist the driver in driving the vehicle in a safer manner.

Example 13 may be example 12, wherein determining a safety related action comprises determining a selected one of having the infotainment system playing soothing music, having the infotainment system provides a reminder to the driver to maintain a safe distance from another vehicle ahead of the vehicle, having the navigation system suggests to the driver to take a break at an upcoming location, or having the navigation system suggesting to the driver to take an alternative route.

Example 14 may be example 12, wherein determining a classification for behavior of a driver of a vehicle comprises determining whether the behavior of the driver belongs to a timid class of behavior, a cautious class of behavior, a conservative class of behavior, a neutral class of behavior, an assertive class of behavior, or an aggressive class of behavior.

Example 15 may be example 14, wherein the timid class of behavior corresponds to behavior of drivers beyond a negative second standard deviation of a driver profile, a cautious class of behavior corresponds to behavior of drivers between a negative first standard deviation and the negative second standard deviation of the driver profile, the conservative class of behavior corresponds to behavior of drivers between an average and the negative first standard deviation of the driver profile, the neutral class of behavior corresponds to behavior of drivers between the mean and a positive first standard deviation of the driver profile, an assertive class of behavior corresponds to behavior of drivers between the positive first standard deviation and a positive second standard deviation of the driver profile, and the aggressive class of behavior corresponds to behavior of drivers beyond the positive second standard deviation of the driver profile.

Example 16 may be example 12, further comprising determining the current level of stress or drowsiness based at least in part on physiological data of the driver collected in real time.

Example 17 may be any one of examples 12-16, wherein determining a classification for behavior of a driver of a vehicle comprises determining the classification for behavior of a driver of a vehicle using a selected one of a multilayer feedforward neural network, a convolution neural network or a recurrent neural network.

Example 18 may be at least one computer readable media (CRM) comprising a plurality of instructions arranged to cause an in-vehicle system disposed in a vehicle, in response to execution of the instructions by a processor of the in-vehicle system, to: determine a classification for behavior of a driver of the vehicle, based at least in part on data about the vehicle collected in real time, and a current level of stress or drowsiness of the driver determined in real time; and determine a safety related action to be performed by an infotainment system or a navigation system of the vehicle to assist the driver in driving the vehicle in a safer manner, based at least in part on the determined driver behavior classification and data related to current traffic or road condition of a route the vehicles is currently traveling on.

Example 19 may be example 18, wherein to determine a safety related action comprises to determine a selected one of the infotainment system playing soothing music, the infotainment system providing a reminder to the driver to maintain a safe distance from another vehicle ahead of the vehicle, the navigation system suggesting to the driver to take a break at an upcoming location, or the navigation system suggesting to the driver to take an alternative route.

Example 20 may be example 18, wherein to determine a classification for behavior of a driver of the vehicle comprises to determine the behavior of the driver to belong to a timid class of behavior, a cautious class of behavior, a conservative class of behavior, a neutral class of behavior, an assertive class of behavior, or an aggressive class of behavior.

Example 21 may be example 20, wherein the timid class of behavior corresponds to behavior of drivers beyond a negative second standard deviation of a driver profile, a cautious class of behavior corresponds to behavior of drivers between a negative first standard deviation and the negative second standard deviation of the driver profile, the conservative class of behavior corresponds to behavior of drivers between an average and the negative first standard deviation of the driver profile, the neutral class of behavior corresponds to behavior of drivers between the mean and a positive first standard deviation of the driver profile, an assertive class of behavior corresponds to behavior of drivers between the positive first standard deviation and a positive second standard deviation of the driver profile, and the aggressive class of behavior corresponds to behavior of drivers beyond the positive second standard deviation of the driver profile.

Example 22 may be example 18, wherein the in-vehicle system is further caused to determine the current level of stress or drowsiness based at least in part on physiological data of the driver collected in real time.

Example 23 may be example 22, wherein to determine a classification for behavior of a driver of a vehicle comprises to determine the classification for behavior of the driver of the vehicle using a selected one of a multilayer feedforward neural network, a convolution neural network or a recurrent neural network.

Example 24 may be any one of examples 18-23, wherein the in-vehicle system is further caused to receive the physiological data of the driver from a wearable device worn by the driver, to receive the data about the vehicle collected in real time from a plurality of sensors of the vehicle, or to receive the data related to current traffic or road condition of the route the vehicle is currently traveling on from one or more cloud servers.

Example 25 may be example 24, wherein the physiological data of the driver comprises galvanic skin response data, components of galvanic skin response data, heart rate or electrocardiogram data of the driver.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second or third) for identified elements are used to distinguish between the elements, and do not indicate or imply a required or limited number of such elements, nor do they indicate a particular position or order of such elements unless otherwise specifically stated.

What is claimed is:

1. An apparatus for computer-assisted driving, comprising:
   a communication interface to receive, from a wearable device worn by a driver of a vehicle, a current level of stress or drowsiness of the driver, wherein the wearable device includes a first multilayer neural network to locally determine the current level of stress or drowsiness of the driver, based at least in part on physiological data of the driver collected in real time by the wearable device worn by the driver;
   a second multilayer neural network implemented with a hardware accelerator in the vehicle and coupled with the communication interface to locally determine a classification for behavior of the driver among a spectrum of behavior classifications, based at least in part on operational data about the vehicle collected in real time by sensors of the vehicle, and the current level of stress or drowsiness of the driver determined by the first multi-layer neural network in real time;

a safety action engine operated by a processor in the vehicle and coupled to the second multilayer neural network to determine a safety related action, based at least in part on the determined driver behavior classification and data related to current traffic or road condition of a route the vehicle is currently traveling on; and an infotainment system or a navigation system disposed in the vehicle to perform the safety related action to assist the driver in driving the vehicle in a safer manner.

2. The apparatus of claim 1, wherein the safety related action comprises a selected one of the infotainment system playing soothing music, the infotainment system providing a reminder to the driver to maintain a safe distance from another vehicle ahead of the vehicle, the navigation system suggesting to the driver to take a break at an upcoming location, or the navigation system suggesting to the driver to take an alternative route.

3. The apparatus of claim 1, wherein the second multilayer neural network is arranged to determine whether the classification for behavior of the driver belong to a timid class of behavior, a cautious class of behavior, a conservative class of behavior, a neutral class of behavior, an assertive class of behavior, or an aggressive class of behavior.

4. The apparatus of claim 3, wherein the timid class of behavior corresponds to behavior of drivers beyond a negative second standard deviation of a driver profile, the cautious class of behavior corresponds to behavior of drivers between a negative first standard deviation and the negative second standard deviation of the driver profile, the conservative class of behavior corresponds to behavior of drivers between an average and the negative first standard deviation of the driver profile, the neutral class of behavior corresponds to behavior of drivers between the average and a positive first standard deviation of the driver profile, the assertive class of behavior corresponds to behavior of drivers between the positive first standard deviation and a positive second standard deviation of the driver profile, and the aggressive class of behavior corresponds to behavior of drivers beyond the positive second standard deviation of the driver profile.

5. The apparatus of claim 1, wherein at least one of the first multilayer neural network or the second multilayer neural network is a selected one of a feedforward neural network, a convolution neural network or a recurrent neural network.

6. The apparatus of claim 1, further comprising a programmable processor to implement the infotainment system or the navigation system.

7. The apparatus of claim 1, further comprising another communication interface to receive the data related to current traffic or road condition of the route the vehicle is currently traveling on from one or more cloud servers.

8. The apparatus of claim 1, wherein the real-time physiological data of the driver comprises galvanic skin response data, components of galvanic skin response data, heart rate or electrocardiogram data of the driver.

9. The apparatus of claim 1, wherein the sensors of the vehicle include at least a first sensor to sense vehicle speed, a second sensor to sense engine speed, a third sensor to sense throttle position, a fourth sensor to sense engine load, a fifth sensor to sense brake pressure, or a sixth sensor to sense steering wheel angle.

10. The apparatus of claim 1 further comprising the infotainment system or the navigation system.

11. A method for computer assisted driving, comprising:
receiving, from a first multilayer neural network disposed in a wearable device worn by a driver of a vehicle, by a second multilayer neural network disposed in the vehicle, a current level of stress or drowsiness of a driver of the vehicle, based at least in part on physiological data of the driver collected in real time by sensors of the wearable device;

determining locally, with the second multilayer neural network disposed in the vehicle, a classification for behavior of the driver of the vehicle among a spectrum of behavior classifications, based at least in part on operational data about the vehicle collected in real time, and the current level of stress or drowsiness of the driver determined by the first multilayer neural network; and determining locally, with a safety action engine, a safety related action, based at least in part on the determined driver behavior classification and data related to current traffic or road condition of a route the vehicle is currently traveling on;

wherein the determined safety related action assists the driver in driving the vehicle in a safer manner.

12. The method of claim 11, wherein determining a safety related action comprises determining a selected one of having an infotainment system playing soothing music, having the infotainment system provide a reminder to the driver to maintain a safe distance from another vehicle ahead of the vehicle, having a navigation system suggest to the driver to take a break at an upcoming location, or having the navigation system suggesting to the driver to take an alternative route.

13. The method of claim 11, wherein determining the classification for behavior of the driver of the vehicle comprises determining whether the behavior of the driver belongs to a timid class of behavior, a cautious class of behavior, a conservative class of behavior, a neutral class of behavior, an assertive class of behavior, or an aggressive class of behavior.

14. The method of claim 13, wherein the timid class of behavior corresponds to behavior of drivers beyond a negative second standard deviation of a driver profile, the cautious class of behavior corresponds to behavior of drivers between a negative first standard deviation and the negative second standard deviation of the driver profile, the conservative class of behavior corresponds to behavior of drivers between an average and the negative first standard deviation of the driver profile, the neutral class of behavior corresponds to behavior of drivers between the average and a positive first standard deviation of the driver profile, the assertive class of behavior corresponds to behavior of drivers between the positive first standard deviation and a positive second standard deviation of the driver profile, and the aggressive class of behavior corresponds to behavior of drivers beyond the positive second standard deviation of the driver profile.

15. At least one non-transitory computer readable media (CRM) comprising a plurality of instructions arranged to cause an infotainment system or a navigation system of an in-vehicle system disposed in a vehicle, in response to execution of the instructions by a processor of the in-vehicle system, to:
receive from a first multilayer neural network disposed in a wearable device worn by a driver of the vehicle, for a second multilayer neural network of the vehicle, a current level of stress or drowsiness of the driver of the vehicle, determined in real time based at least in part on physiological data of the driver collected in real time by sensors of the wearable device;

receive from the second multilayer neural network of the vehicle a classification for behavior of the driver of the vehicle among a spectrum of behavior classifications, locally determined in real time based at least in part on operational data about the vehicle collected in real time, and the current level of stress or drowsiness of the driver determined by the first multilayer neural network; and determine locally, with a safety action engine, a safety related action to be performed by the infotainment system or the navigation system of the vehicle to assist the driver in driving the vehicle in a safer manner, based at least in part on the classification for behavior of the driver, and data related to current traffic or road condition of a route the vehicle is currently traveling on.

16. The non-transitory CRM of claim 15, wherein to determine a safety related action comprises to determine a selected one of the infotainment system playing soothing music, the infotainment system providing a reminder to the driver to maintain a safe distance from another vehicle ahead of the vehicle, the navigation system suggesting to the driver to take a break at an upcoming location, or the navigation system suggesting to the driver to take an alternative route.

17. The non-transitory CRM of claim 15, wherein the classification for behavior of the driver of the vehicle comprises to determine the behavior of the driver to belong to a timid class of behavior, a cautious class of behavior, a conservative class of behavior, a neutral class of behavior, an assertive class of behavior, or an aggressive class of behavior.

18. The non-transitory CRM of claim 17, wherein the timid class of behavior corresponds to behavior of drivers beyond a negative second standard deviation of a driver profile, the cautious class of behavior corresponds to behavior of drivers between a negative first standard deviation and the negative second standard deviation of the driver profile, the conservative class of behavior corresponds to behavior of drivers between an average and the negative first standard deviation of the driver profile, the neutral class of behavior corresponds to behavior of drivers between the average and a positive first standard deviation of the driver profile, the assertive class of behavior corresponds to behavior of drivers between the positive first standard deviation and a positive second standard deviation of the driver profile, and the aggressive class of behavior corresponds to behavior of drivers beyond the positive second standard deviation of the driver profile.

19. The non-transitory CRM of claim 15, wherein the in-vehicle system is further caused to receive the operational data about the vehicle collected in real time from a plurality of sensors of the vehicle, or to receive the data related to current traffic or road condition of the route the vehicle is currently traveling on from one or more cloud servers.

20. The non-transitory CRM of claim 15, wherein the physiological data of the driver comprises galvanic skin response data, components of galvanic skin response data, heart rate or electrocardiogram data of the driver.

* * * * *